US00PP35009P3

(12) United States Plant Patent
van Langen

(10) Patent No.: US PP35,009 P3
(45) Date of Patent: Feb. 28, 2023

(54) ***ECHEVERIA* PLANT NAMED 'AMIECH2005'**

(50) Latin Name: ***Echeveria* hybrid**
Varietal Denomination: AMIECH2005

(71) Applicant: Novoami B.V., Heerhugowaard (NL)

(72) Inventor: Gerard van Langen, Heerhugowaard (NL)

(73) Assignee: Novoami B.V., Heehugowaard (NL)

( * ) Notice: Subject to any disclaimer, the term of this patent is extended or adjusted under 35 U.S.C. 154(b) by 0 days.

(21) Appl. No.: 17/300,675

(22) Filed: Sep. 21, 2021

(65) Prior Publication Data

US 2022/0167539 P1 May 26, 2022

(30) Foreign Application Priority Data

Nov. 25, 2020 (QZ) ..... PBR 2020/2978

(51) Int. Cl.
*A01H 5/12* (2018.01)
*A01H 6/32* (2018.01)

(52) U.S. Cl.
USPC ..... Plt./373
CPC ..... *A01H 6/32* (2018.05)

(58) Field of Classification Search
USPC ..... Plt./373, 263.1
CPC ... A01H 5/12; A01H 5/02; A01H 5/00; A01H 6/32; A01H 6/00
See application file for complete search history.

*Primary Examiner* — June Hwu
(74) *Attorney, Agent, or Firm* — Samuel R. McCoy, Jr.

(57) ABSTRACT

A new and distinct *Echeveria* hybrid plant named 'AMIECH2005' which is characterized by a relative abundance of long, narrow oblanceolate foliage that is loosely arranged in a basal rosette, green to greyed-green glaucous foliage that is covered with greyed-purple epicuticular wax which gives the foliage a blue-grey appearance, older foliage at the outer whorls of the rosette that has a light greyed-green appearance on the upper surface and an olive-green appearance on the lower surface, foliage that is tipped greyed-purple, and the stability of these characteristics from generation to generation.

4 Drawing Sheets

Latin name of the genus and species: The Latin name of the genus and species of the novel variety disclosed herein is *Echeveria* hybrid.

Variety denomination: The inventive variety of *Echeveria* hybrid disclosed herein has been given the variety denomination 'AMIECH2005'.

CROSS REFERENCE TO RELATED APPLICATIONS

This application claims priority to the Community Plant Variety Rights application number 2020/2978, filed Nov. 25, 2020, which is herein incorporated by reference.

BACKGROUND OF THE INVENTION

Parentage: 'AMIECH2005' is an interspecific hybrid seedling selection resulting from the controlled pollination of an unnamed *Echeveria elegans* plant (not patented), the seed parent, with an *Echeveria carnicolor* x *E. affinis* 'Serrana' plant (not patented), the pollen parent. The crossing was made by the inventor in the summer of 2017 at a commercial greenhouse in Heerhugowaard, the Netherlands. In the autumn of 2018, one seedling was observed which exhibited unique growth and foliage characteristics. The seedling was isolated for further evaluation in order to confirm the distinctness and stability of the characteristics first observed. Upon confirmation of distinctness and stability, 'AMIECH2005' was selected for commercialization.

Asexual Reproduction: Asexual reproduction of the new cultivar 'AMIECH2005', by way of rooting leaf cuttings, was first initiated in the winter of 2018-2019 at the inventor's commercial greenhouse in Heerhugowaard, the Netherlands. Through four subsequent generations, the unique features of this cultivar have proven to be stable and true to type.

SUMMARY OF THE INVENTION

The cultivar 'AMIECH2005' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'AMIECH2005'. These characteristics in combination distinguish 'AMIECH2005' as a new and distinct *Echeveria* hybrid cultivar:

1. 'AMIECH2005' exhibits a flattened to flattened globular plant profile with foliage loosely arranged in a basal rosette; and
2. 'AMIECH2005' exhibits a relative abundance of long, narrow oblanceolate foliage that is curled upward towards the apex of the lamina; and
3. 'AMIECH2005' exhibits green to greyed-green juvenile and mature foliage that is covered with a layer of greyed-purple epicuticular wax which gives the foliage a blue-grey appearance; and 4. 'AMIECH2005' exhibits an epicuticular waxy layer on the adaxial surface of the mature foliage that becomes progressively thinner towards the outermost whorls of the rosette, giving the oldest foliage a light greyed-green general appearance; and
5. 'AMIECH2005' exhibits older foliage at the outermost whorls of the rosette that is lightly suffused with greyed-orange on the distal portion of the adaxial surface, with a very thin layer of epicuticular wax, giving the foliage an olive-green general appearance; and
6. 'AMIECH2005' exhibits margins of the mature foliage in the outermost whorls of the rosette that are occasionally lightly suffused with greyed-orange, distally; and
7. 'AMIECH2005' exhibits juvenile and mature foliage that is tipped greyed-purple.

BOTANICAL DESCRIPTION OF THE PLANT

Figure 1:
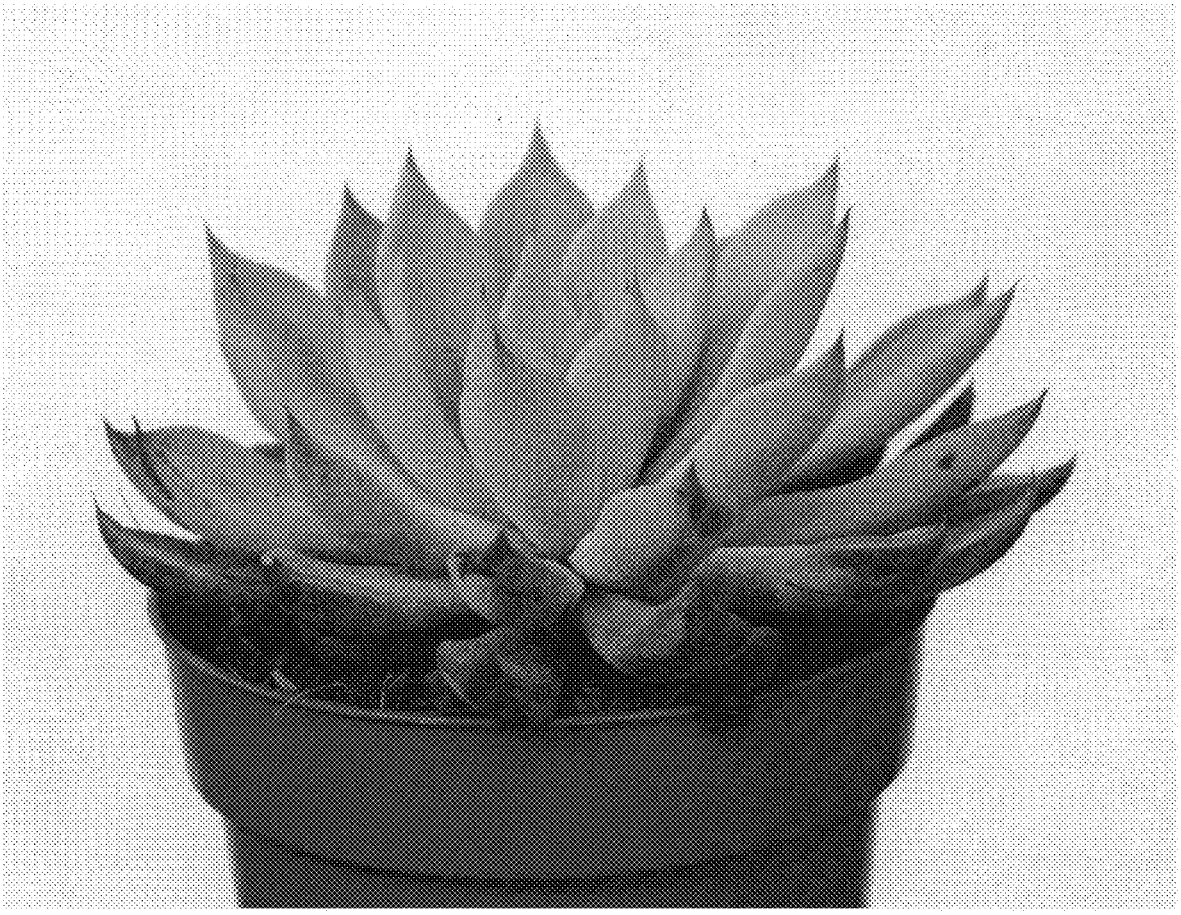
FIG. 1 illustrates, as nearly true as it is reasonably possible to make the same in color photographs of this type, an exemplary plant of 'AMIECH2005' grown in a commercial greenhouse in Heerhugowaard, the Netherlands. This plant is approximately 20 week-old, shown planted in an 8.5 cm container.
Figure 2:
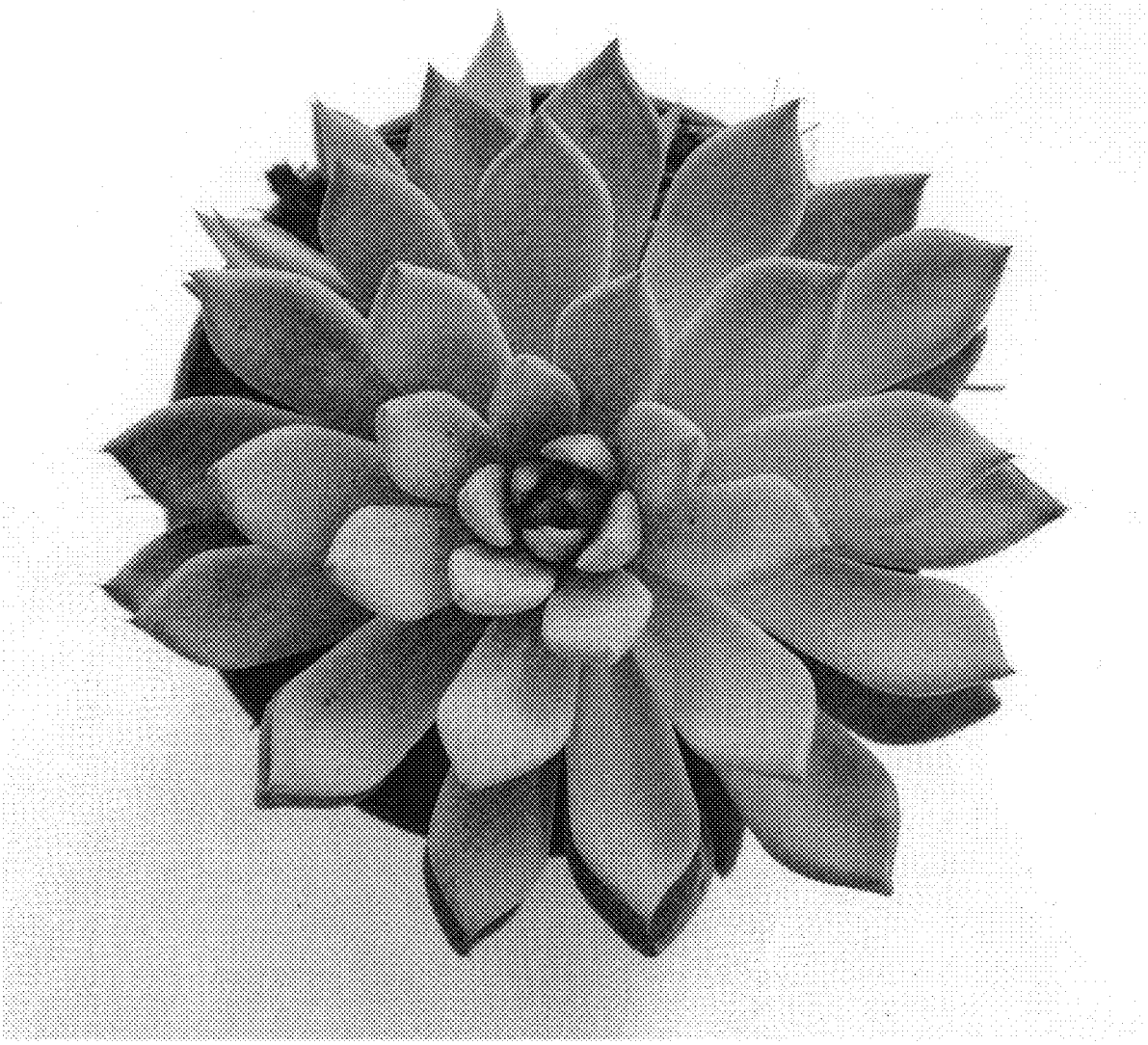
FIG. 2 illustrates, as nearly true as it is reasonably possible to make the same in color photographs of this type, the typical foliage arrangement of 'AMIECH2005'.
Figure 3:
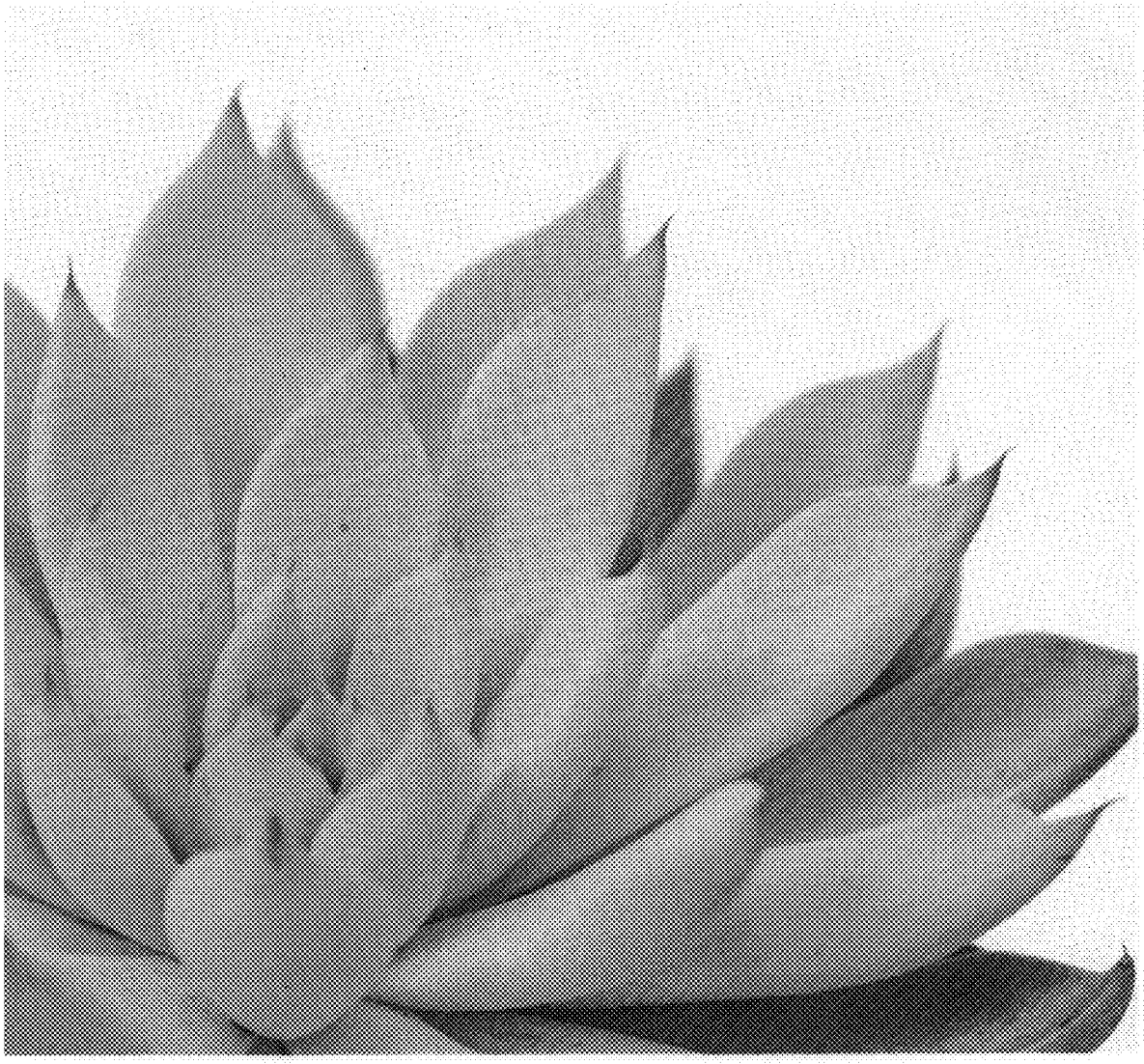
FIG. 3 illustrates, as nearly true as it is reasonably possible to make the same in color photographs of this type, the adaxial surface of the mature foliage 'AMIECH2005'.
Figure 4:
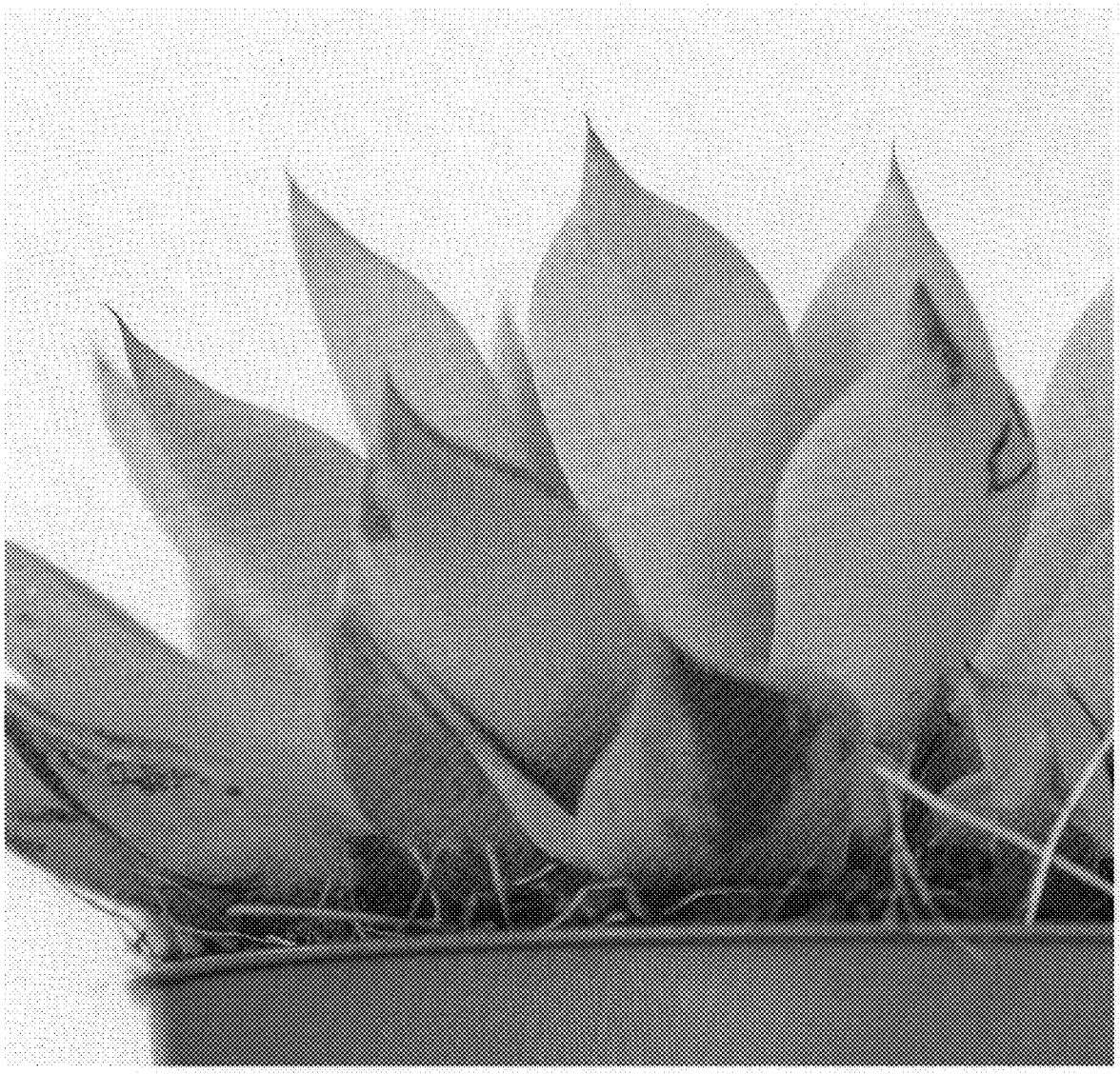
FIG. 4 illustrates, as nearly true as it is reasonably possible to make the same in color photographs of this type, the abaxial surface of the mature foliage 'AMIECH2005'.

The following observations and measurements made in June of 2021 describe averages from a sample set of six specimens of 20 week-old 'AMIECH2005' plants grown in 8.5 cm nursery containers at commercial greenhouse in Heerhugowaard, the Netherlands. Plants were produced using conventional greenhouse production protocols for *Echeveria* plants which consisted of minimal irrigation and fertilizer applications, and chemical pest and disease control measures against mealy bug and *Botrytis* as required. Plants were grown under approximately 50 percent shade after propagation and later exposed to full sun once they began to mature. No photoperiodic treatments or artificial light was given to the plants.

Those skilled in the art will appreciate that certain characteristics will vary with older or, conversely, with younger plants. 'AMIECH2005' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart*, The Royal Horticultural Society, London, 2015 (sixth edition).

A botanical description of 'AMIECH2005' and comparisons with the parent plants and closest known comparator are provided below.

Plant description:

*Growth habit*.—Succulent perennial with foliage growing in a non-branched basal rosette.

*Plant shape*.—Flattened to flattened globular.

*Height from soil level to top of foliar plane*.—5.1 cm.

*Plant spread*.—Average of 10.4 cm.

*Growth rate*.—Moderately fast growing.

*Plant vigor*.—Moderately vigorous.

*Propagation*.—Type — Leaf cuttings. Time to initiate rooting — Approximately 21 days at 18 degrees Celsius. Crop time — Approximately 35 weeks to produce a marketable plant in an 8.5 cm container.

*Disease and pest resistance or susceptibility*.—Neither resistance nor susceptibility to typical *Echeveria* pests and diseases has been observed.

*Environmental tolerances*.—Adapt to, at least, USDA Zones 10 to 12 and temperatures as high as 40 degrees Celsius; moderate tolerance to rain yet drought tolerant once established; high tolerance to wind.

Root system:

*General*.—Fine, well-branched fibrous roots.

Stems:

*Branching habit*.—Leaves in a non-branching basal rosettes; no main branches or lateral branches present.

Foliage:

*Arrangement*.—Rosette.

*Division*.—Simple.

*Attachment*.—Sessile.

*Quantity*.—Approximately 50 leaves per rosette.

*Shape*.—Oblanceolate.

*Dimensions*.—5.0 cm long, 1.45 cm wide, and 0.6 cm thick, on average.

*Aspect*.—Slightly concave with leaf tips slightly curled upward at an approximate angle of 45 degrees to the lamina.

*Attitude*.—Juvenile foliage at the center of the rosette is held upright; foliage becomes progressively more relaxed towards the outer whorls of mature foliage; mature foliage is held at approximately 35 degrees to horizontal.

*Apex*.—Apiculate.

*Base*.—Cuneate.

*Margin*.—Entire; margins are not undulate.

*Pubescence, texture and luster of the adaxial surface; juvenile foliage*.—Smooth, glabrous, and moderately to strongly glaucous.

*Pubescence, texture and luster of the abaxial surface; juvenile foliage*.—Smooth, glabrous, and moderately to strongly glaucous.

*Pubescence, texture and luster of the adaxial surface; mature foliage*.—Smooth, glabrous, and moderately glaucous; the epicuticular waxy layer becomes progressively thinner towards the outer whorls of the rosette.

*Pubescence, texture and luster of the abaxial surface; mature foliage*.—Smooth, glabrous, and moderately glaucous; the epicuticular waxy layer becomes progressively thinner towards the outer whorls of the rosette.

*Luster of the adaxial surface*.—Matte.

*Luster of the abaxial surface*.—Matte.

*Color*.—Juvenile foliage, adaxial surface — Nearest to a mixture of green and greyed-green, RHS 137D and 191A yet nearest to 191A tipped with greyed-purple, nearest to RHS 185D. The epicuticular glaucous wax covering the leaf surface is greyed-green, nearest to RHS 188A. Juvenile foliage, abaxial surface — Greyed-green, nearest to RHS 191B; tipped with greyed-purple, nearest to RHS 185D. The epicuticular glaucous wax covering the leaf surface is greyed-green, nearest to RHS 188B. Mature foliage, adaxial surface — Nearest to a mixture of green and greyed-green, RHS NN138B and 191A yet nearest to 191A; fading to yellow-green towards the base, nearest to RHS 147C; on occasion, the margins are very lightly suffused with greyed-orange towards the apex, nearest to a mixture of RHS 174C and 174D; tipped with greyed-purple, nearest to RHS 185B. The epicuticular glaucous wax covering the leaf surface is greyed-green, nearest to RHS 188A. The epicuticular waxy layer on the oldest leaves in the outermost whorls of the rosette is very thin. Mature foliage, abaxial surface — Greyed-green, nearest to a mixture of RHS 191A and 191B, and lightly suffused with greyed-orange distally, nearest to RHS 174C; fading to yellow-green towards the base, nearest to RHS 148C; on occasion, the margins are very lightly suffused with greyed-orange towards the apex, nearest to a mixture of RHS 174C and 174D; tipped with greyed-purple, nearest to RHS 185B. The epicuticular glaucous wax covering the leaf surface is greyed-green, nearest to RHS 188B. The epicuticular waxy layer on the oldest leaves in the outermost whorls of the rosette is very thin. Venation, adaxial surface — No visible venation. Venation, abaxial surface — No visible venation.

*Petiole*.—No petiole; leaves are sessile.

Inflorescence: No flowering has been observed to date.

COMPARISONS WITH THE PARENT PLANTS AND CLOSEST KNOWN COMPARATOR

Plants of the new cultivar 'AMIECH2005' differ from the seed parent, an unnamed *Echeveria elegans* plant (not patented), in the following characteristics described in Table 1 below.

TABLE 1

| Characteristic | 'AMIECH2005' | The seed parent. |
|---|---|---|
| Plant size. | Larger than the seed parent. | Smaller than 'AMIECH2005'. |
| Foliage dimensions. | Longer and narrower than the seed parent. | Shorter and broader than 'AMIECH2005'. |
| General coloration of the foliage. | Green to greyed-green and covered with a layer of greyed-purple epicuticular wax which gives the foliage a blue-grey appearance; tipped greyed-purple. | Green and covered with a relatively thick layer of greyed-green epicuticular wax which give the foliage a bluish hue. |

Plants of the new cultivar 'AMIECH2005' differ from the pollen parent, an *Echeveria carnicolor* x *E. affinis* 'Serrana' plant (not patented), in the following characteristics described in Table 2 below.

TABLE 2

| Characteristic | 'AMIECH2005' | 'Serrana' |
|---|---|---|
| Foliage abundance. | More abundant than 'Serrana'. | Less abundant than 'AMIECH2005'. |
| Foliage dimensions. | Longer and narrower than 'Serrana'. | Shorter and broader than 'AMIECH2005'. |
| General coloration of the foliage. | Green to greyed-green and covered with a layer of greyed-purple epicuticular wax which gives the foliage a blue-grey appearance; tipped greyed-purple. | Green and heavily suffused with a mixture of very dark brown and greyed-purple; tipped black. |

COMPARISONS WITH THE CLOSEST KNOWN COMPARATOR

Plants of the new cultivar 'AMIECH2005' differ from the closest known commercial comparator, *Echeveria* hybrid 'Silver Queen' (not patented), in the following characteristics described in Table 3 below.

TABLE 3

| Characteristic | 'AMIECH2005' | 'Silver Queen' |
|---|---|---|
| Foliage abundance. | More abundant than 'Silver Queen'. | Less abundant than 'AMIECH2005'. |
| Foliage dimensions. | Longer and narrower than 'Silver Queen'. | Shorter and broader than 'AMIECH2005'. |

TABLE 3-continued

| Characteristic | 'AMIECH2005' | 'Silver Queen' |
|---|---|---|
| General coloration of the foliage. | Green to greyed-green and covered with a layer of greyed-purple epicuticular wax which gives the foliage a blue-grey appearance; tipped greyed-purple. | Greyed-green, suffused with greyed-purple. |

That which is claimed is:

1. A new and distinct variety of *Echeveria* hybrid plant named 'AMIECH2005', substantially as described and illustrated herein.

* * * * *